United States Patent [19]

Petrillo, Jr.

[11] 4,070,361
[45] Jan. 24, 1978

[54] MERCAPTOALKYLSULFONYL PROLINE AND PIPECOLIC ACID AND ESTERS THEREOF

[75] Inventor: Edward William Petrillo, Jr., Pennington, N.J.

[73] Assignee: E. R. Squibb & Sons, Inc., Princeton, N.J.

[21] Appl. No.: 789,466

[22] Filed: Apr. 21, 1977

[51] Int. Cl.² ............... C07D 207/48; C07D 211/96
[52] U.S. Cl. .................. 260/293.85; 260/293.73; 260/326.2; 260/326.47
[58] Field of Search .............. 260/293.85, 293.73, 260/326.2, 326.47

[56] References Cited

U.S. PATENT DOCUMENTS

| 3,086,974 | 4/1963 | Schlor et al. | 260/293.73 |
| 3,453,312 | 7/1969 | Sprague et al. | 260/293.73 |
| 3,867,390 | 2/1975 | Cross et al. | 260/293.73 |

Primary Examiner—Henry R. Jiles
Assistant Examiner—Richard A. Schwartz
Attorney, Agent, or Firm—Lawrence S. Levinson; Merle J. Smith

[57] ABSTRACT

Mercaptoalkylsulfonyl proline derivatives and related compounds which have the general formula

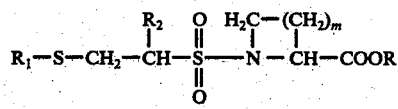

are useful as hypotensive agents.

12 Claims, No Drawings

MERCAPTOALKYLSULFONYL PROLINE AND PIPECOLIC ACID AND ESTERS THEREOF

SUMMARY OF THE INVENTION

This invention relates to new mercaptoalkylsulfonyl proline derivatives and related compounds which have the formula

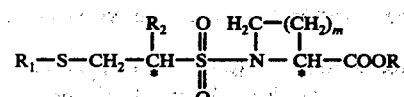

R and $R_2$ each is hydrogen or lower alkyl.
$R_1$ is hydrogen, lower alkanoyl or benzoyl.
m is 2 or 3.

DETAILED DESCRIPTION OF THE INVENTION

In formula I, the lower alkyl groups represented by R and $R_2$ are straight or branched chain aliphatic hydrocarbon groups having up to seven carbon atoms, for example, methyl, ethyl, propyl, isopropyl, butyl, sec.butyl, t-butyl and the like. The $C_1$–$C_4$ members and especially the $C_1$–$C_2$ members are preferred.

The lower alkanoyl groups represented by $R_1$ are the acyl radicals of the lower fatty acids (up to seven carbons) such as acetyl, propionyl, butyryl, isobutyryl and the like. Those having up to four carbons are preferred. Acetyl is especially preferred.

Preferred embodiments of this invention are those compounds of formula I wherein m is 2, R and $R_2$ each is hydrogen and $R_1$ is hydrogen or lower alkanoyl, especially hydrogen or acetyl.

The compounds of this invention are produced by the following sequence of reactions.

Proline or pipecolic acid, preferably in the form of a lower alkyl ester in which the alkyl group is easily removed, e.g., the t-butyl ester, is made to react with a haloalkylsulfonyl halide of the formula

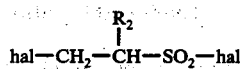

wherein hal represents halogen, preferably chlorine or bromine, in the presence of an organic base like triethylamine, N,N-dimethylaniline, N-methylmorpholine or the like and in an inert organic solvent like dichloromethane, ether, tetrahydrofuran, dioxane or the like. This coupling reaction yields a compound of the formula

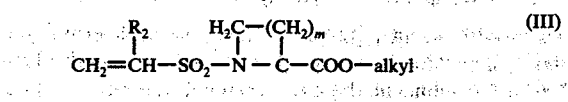

Reaction of the compound of formula III with a compound of the formula

in the presence of an organic base like those referred to above and in an organic solvent like ether, tetrahydrofuran, dioxane, or the like, yields a product of the formula

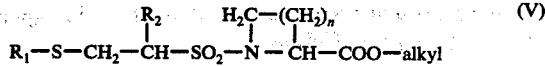

Treatment of the product of formula V with trifluoroacetic acid and anisole, when the alkyl group is t-butyl removes the ester group and yields the free acid of formula I, i.e., wherein R is hydrogen.

Treatment of the product of formula V with sodium or potassium hydroxide in water or a lower alcohol, when the alkyl group is methyl or other lower alkyl group, and $R_1$ is lower alkanoyl or benzoyl, removes the ester group and the $R_1$ group and yields, after acidification, the free acid of formula I, i.e., wherein R and $R_1$ are hydrogen.

Preferably, the thiol of formula IV is one in which $R_1$ is lower alkanoyl or benzoyl, e.g., thiolacetic acid, thiolbenzoic acid or the like with the result that $R_1$ in the product of formula V is lower alkanoyl or benzoyl. A product of formula I wherein $R_1$ is hydrogen is obtained by treating the product of formula V, either before or after the removal of the ester group, if desired, with ammonia or concentrated ammonium hydroxide solution.

The proline and pipecolic acid esters are produced as described in copending application Ser. No. 657,792 filed Feb. 13, 1976 by Miguel Angel Ondetti and David W. Cushman.

The asterisks in formula I indicate asymmetric carbon atoms (the carbon atom bearing $R_2$ is asymmetric when $R_2$ is other than hydrogen). Preferred are those compounds wherein the proline or pipecolic acid portion of the molecule is in the L-form.

Additional experimental details are provided in the illustrative examples which follow below.

The compounds of this invention are angiotensin converting enzyme inhibitors and are useful as hypotensive agents, particularly for the reduction of angiotensin dependent hypertension. By administering a composition containing one or a combination of angiotensin converting enzyme inhibitors this invention to a hypertensive mammal, it intervenes in the renin → angiotensin I → angiotensin II sequence and the hypertension is reduced or alleviated.

A single dose, or preferably two to four divided daily doses, provided on a basis of about 1 to 1000 mg. per kilogram per day and especially about 10 to 200 mg. per kilogram per day and especially about 10 to 200 mg. per kilogram per day is appropriate to bring about a reduction in elevated blood pressure. The animal model experiments described by Engel., Proc. Soc. Exp. Biol. Med. 143, 483 (1973) provide a valuable guide.

The composition is preferably administered orally, but it can also be administered subcutaneously, intramuscularly, intravenously or intraperitoneally. The compound or compounds of formula I can be formulated as tablets, capsules or elixirs for oral administration. Sterile solutions or suspensions can be used for parenteral use.

About 50 to 1500 mg. of a compound or compounds of formula I can be compounded with a physiologically acceptable vehicle, carrier, excipient, binder, preservative, stabilizer, flavor, etc., in a conventional unit dosage form as called for by accepted pharmaceutical practice. The amount of active substance is selected so as to provide a dosage in the range indicated.

The following examples are illustrative of the invention and represent preferred embodiments. All temperatures are in degrees Celsius.

EXAMPLE 1

1-[[2-(Acetylthio)ethyl]sulfonyl]-L-proline a. 1-(Vinylsulfonyl)-L-proline t-butyl ester L-Proline t-butyl ester (6.9 g. 0.04 mol.) and triethylamine (14 ml., 0.1 mol.) are dissolved in 200 ml. of dichloromethane and stirred in an ice bath while 2-chloroethanesulfonyl chloride (8.2 g., 0.05 mol.) in 100 ml. of dichloromethane is added over 20 minutes. After stirring 2 hours, the mixture is washed with 5% potassium bisulfate solution, saturated sodium bicarbonate solution and brine, then evaporated in vacuo. The semi-solid residue is chromatographed on 350 ml. silica gel using 1:1 ethyl acetate/hexane as eluant. The main fraction, comprising 1-(vinylsulfonyl)-L-proline t-butyl ester is crystallized from ether/hexane, m.p. 84°–87° (7.1 g., 68%).

b. 1-[[2-(Acetylthio)ethyl]sulfonyl]-L-proline t-butyl ester 1-(Vinylsulfonyl)-L-proline t-butyl ester (5.0 g., 0.0192 mol.), triethylamine (2.8 ml., 0.02 mol.) and thiolacetic acid (1.43 ml., 0.02 mol.) are mixed in 100 ml. of ether and allowed to stand overnight. The mixture is washed with 5% potassium bisulfate solution, saturated sodium bicarbonate solution and brine, then evaporated in vacuo to a yellow oil. The procedure is repeated using half of the above quantities of triethylamine and thiolacetic acid. Workup as in part a affords the crude product, 1-[[2-(acetylthio)ethyl]-sulfonyl-L-proline t-butyl ester, which is filtered through a short silica gel column and crystallized from ether/hexane, m.p. 46°–50° (2.9 g., 45%)

c. 1-[[2-Acetylthio)ethyl]sulfonyl]-L-proline

The t-butyl ester from part b (2.9 g., 0.0086 mol.) is dissolved in 15 ml. of anisole and 45 ml. of trifluoroacetic acid and let stand 1 hour. The mixture is evaporated in vacuo to a gummy residue which is taken up in ethyl acetate and treated with a large volume of hexane. The supernatant is decanted, and the procedure repeated. The resulting semi-solid is crystallized from ethyl acetate-hexane, m.p. 63°–67° (1.9 g., 78%). $[\alpha]_D = -59.3$, $c = 1.07\xi$, dimethylformamide.

EXAMPLE 2

1-[(2-Mercaptoethyl)sulfonyl]-L-proline

1-[[2-(Acetylthio)ethyl]sulfonyl]-L-proline (640 mg., 0.0023 mol.) is dissolved in 5 ml. of water and 5 ml. of concentrated ammonia and stirred 1 hour under nitrogen. The solution is acidified with concentrated hydrochloric acid, extracted with ethyl acetate, and the extracts are washed with brine, dried (MgSO$_4$) and evaporated to an oily residue which is applied to a 75 ml. silica gel column. Elution with 10% acetic acid/benzene affords a main fraction which is crystallized from chloroform/hexane, to obtain 440 mg. (81%) of 1-[(2-mercaptoethyl)sulfonyl]-L-proline, m.p. 99°–101° $[\alpha]_D = -64.3°$, $c = 1.1\xi$, dimethylformamide.

EXAMPLE 3

1-[[2-(Benzoylthio)ethyl]sulfonyl]-L-proline

By substituting thiobenzoic acid for thiolacetic acid in the procedure of Example 1b, and then submitting the product to the procedure of Example 1c, 1-[[2-(benzoylthio)ethyl]sulfonyl]-L-proline is obtained.

EXAMPLE 4

1-[[2-(Acetylthio)ethyl]sulfonyl]-L-pipecolic acid a. 1-(Vinylsulfonyl)-L-pipecolic acid By substituting L-pipecolic acid t-butyl ester for the L-proline t-butyl ester in the procedure of Example 1a, 1-(vinylsufonyl)-L-pipecolic acid t-butyl ester is obtained.

b. 1-[[2-(Acetylthio)ethyl]sulfonyl]-L-pipecolic acid

By substituting 1-(vinylsulfonyl)-L-pipecolic acid t-butyl ester for the 1-(vinylsulfonyl)-L-proline t-butyl ester in the procedure of Example 1b, and then submitting the product to the procedure of Example 1c, 1-[[2-acetylthio)-ethyl]sulfonyl]-L-pipecolic acid t-butyl ester and 1-[[2-(acetylthio)ethyl]sulfonyl]-L-pipecolic acid are obtained.

EXAMPLE 5

1-[(2-Mercaptoethyl)sulfonyl]-L-pipecolic acid

By substituting 1-[[2-(acetylthio)ethyl]sulfonyl]-L-pipecolic acid for the 1-[[2-(acetylthio)ethyl]sulfonyl]-L-proline in the procedure of Example 2, 1-[(2-mercaptoethyl)-sulfonyl]-L-pipecolic acid is obtained.

EXAMPLE 6

1-[[2-(Benzoylthio)ethyl]sulfonyl]-L-pipecolic acid

By substituting 1-(vinylsulfonyl)-L-pipecolic acid t-butyl ester for the 1-(vinylsulfonyl)-L-proline t-butyl ester in the procedure of Example 3, 1-[[2-benzoylthio)ethyl]-sulfonyl]-L-pipecolic acid is obtained.

EXAMPLE 7

1-[[2-(Acetylthio)-1-methylethyl]sulfonyl]-L-proline a. 1-(2-Propenylsulfonyl)-L-proline t-butyl ester By substituting 1-chloro-2-propanesulfonyl chloride for the 2-chloroethanesulfonyl chloride in the procedure of Example 1a, 1-(2-propenylsulfonyl)-L-proline t-butyl ester is obtained.

b. 1-[[2-(Acetylthio)-1-methylethyl]sulfonyl]-L-proline

By substituting 1-[2-propenylsulfonyl]-L-proline t-butyl ester for the 1-(vinylsulfonyl)-L-proline t-butyl ester in the procedure of Example 1b, and then submitting the product to the procedure of Example 1c, 1-[[2-(acetylthio)-1-methylethyl]sulfonyl]-L-proline t-butyl ester and 1-[[2-(acetylthio)-1-methylethyl]sulfonyl]-L-proline are obtained.

EXAMPLE 8

1-[(2-Mercapto-1-methylethyl)sulfonyl]-L-proline

By substituting 1-[[2-(Acetylthio)-1-methylethyl]-sulfonyl]-L-proline for the 1-[[2-(acetylthio)ethyl]sulfonyl]-L-proline in the procedure of Example 2, 1-[2-mercapto-1-methylethyl)sulfonyl]-L-proline is obtained.

EXAMPLE 9

1-[[2-(Benzoylthio)-1-methylethyl]sulfonyl]-L-proline

By substituting 1-(2-propenylsulfonyl)-L-proline t-butyl ester for the 1-(vinylsulfonyl)-L-proline t-butyl ester in the procedure of Example 3, 1-[[2-(benzoylthio)-1-methylethyl]sulfonyl]-L-proline is obtained.

EXAMPLE 10

1-[[2-(Acetylthio)-1-methylethyl]sulfonyl]-L-pipecolic acid a. 1-(2-Propenylsulfonyl)-L-pipecolic acid t-butyl ester By substituting 1-chloro-2-propanesulfonyl chloride for the 2-chloroethanesulfonyl chloride and L-pipecolic acid t-butyl ester for L-proline t-butyl ester in the procedure of Example 1a, 1-(2-propenylsulfonyl)-L-pipecolic acid t-butyl ester is obtained.

b. 1-[[2-(Acetylthio)-1-methylethyl]sulfonyl]-L-pipecolic acid

By substituting 1-(2-propenylsulfonyl)-L-pipecolic acid t-butyl ester for the 1-(vinylsulfonyl)-L-proline t-butyl ester in the procedure of Example 1b, and then submitting the product to the procedure of Example 1c, 1-[[2-(acetylthio)-1-methylethyl]sulfonyl]-L-pipecolic acid t-butyl ester and 1-[[2-(acetylthio)-1-methylethyl]sulfonyl]-L-pipecolic acid are obtained.

EXAMPLE 11

1-[(2-Mercapto-1-methylethyl)sulfonyl]-L-pipecolic acid

By substituting 1-[[2-(acetylthio)-1-methylethyl]-sulfonyl]-L-pipecolic acid for the 1-[[2-(acetylthio)ethyl]-sulfonyl]-L-proline in the procedure of Example 2, 1-[(2-mercapto-1-methylethyl)sulfonyl]-L-pipecolic acid is obtained.

What is claimed is:

1. A compound of the formula

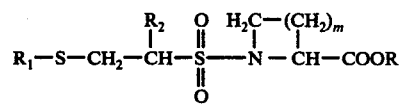

wherein
R and $R_2$ each is hydrogen or lower alkyl;
$R_1$ is hydrogen, lower alkanoyl or benzoyl; and
$m$ is 2 or 3.

2. A compound as in claim 1 wherein R is hydrogen.
3. A compound as in claim 1 wherein $m$ is 2.
4. A compound as in claim 1 wherein $m$ is 3.
5. A compound as in claim 1 wherein R and $R_2$ each is hydrogen.
6. A compound as in claim 1 wherein $m$ is 2, R and $R_2$ each is hydrogen and $R_1$ is hydrogen or lower alkanoyl.
7. A compound as in claim 6 wherein the lower alkanoyl group is acetyl.
8. The L-form of the compound of claim 6.
9. A compound as in claim 6 wherein $R_1$ is hydrogen.
10. The L-form of the compound of claim 9.
11. A compound as in claim 1 wherein R and $R_2$ each is hydrogen, $R_1$ is benzoyl and $m$ is 2.
12. A compound as in claim 1 wherein R, $R_1$ and $R_2$ each is hydrogen and $m$ is 3.

* * * * *